(12) United States Patent
Beer et al.

(10) Patent No.: US 6,204,284 B1
(45) Date of Patent: Mar. 20, 2001

(54) USE OF 1-(SUBSTITUTEDPHENYL)-3-AZABICYCLO[3.1.0]HEXANES FOR THE TREATMENT OF CHEMICAL DEPENDENCIES

(75) Inventors: Bernard Beer, Cliffside Park, NJ (US); Joseph William Epstein, Monroe, NY (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 08/414,180

(22) Filed: Mar. 31, 1995

Related U.S. Application Data

(63) Continuation of application No. 08/122,856, filed on Sep. 16, 1993, now abandoned, which is a continuation of application No. 07/811,418, filed on Dec. 20, 1991, now abandoned.

(51) Int. Cl.[7] .................................................. A61K 31/40
(52) U.S. Cl. .......................... 514/412; 514/811; 514/812
(58) Field of Search .................................... 514/412, 811, 514/812

(56) References Cited

U.S. PATENT DOCUMENTS 4,435,419    3/1984    Epstein et al. .................. 424/274

OTHER PUBLICATIONS

Amit et al., J. Clin. Psychiatry, 52:12(suppl), Dec. 1991.

*Primary Examiner*—Russell Travers
*Assistant Examiner*—Shengjun Wang
(74) *Attorney, Agent, or Firm*—Rebecca R. Barrett

(57) ABSTRACT

The invention is a method of treatment for the relief of an addictive, compulsive disorder which comprises the administration to a human or animal suffering from such a disorder an effective amount of the compound of the formula:

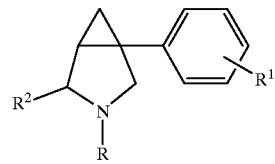

wherein R is hydrogen, alkyl ($C_1$–$C_6$); $R^1$ is hydrogen, mono or disubstituted halogen, alkoxy ($C_1$–$C_3$), $CF_3$, alkyl ($C_1$–$C_6$); and $R^2$ is hydrogen, methyl or ethyl, or a pharmaceutically acceptable salt thereof.

24 Claims, No Drawings

USE OF 1-(SUBSTITUTEDPHENYL)-3-AZABICYCLO[3.1.0]HEXANES FOR THE TREATMENT OF CHEMICAL DEPENDENCIES

This application is a continuation of application Ser. No. 08/122,856 filed Sep. 16, 1993, now abandoned, which is a continuation of Ser. No. 07/811,418, filed Dec. 20, 1991 now abandoned.

BACKGROUND OF THE INVENTION

1. Field of the Invention

The present invention is concerned with treating a chemically dependent mammal with a 1-(substitutedphenyl)-3-azabicyclo[3.1.0]hexane in order to reduce or alleviate the dependency.

2. Description of the Prior Art

A series of 1-(substitutedphenyl)-3-azabicyclo[3.1.0] hexanes are described in U.S. Pat. Nos. 4,088,652; 4,118,393; 4,118,417; 4,131,611; 4,196,120 and 4,231,935. In U.S. Pat. No. 4,435,419 a method of treating depression and stress in warm-blooded blooded animals is described.

Chemical dependency in a mammal is the abnormal craving or desire for, or an addiction to a drug. The drug can encompass alcohol or any of the legal prescription medications as well as those compounds such as cocaine and heroin which are sold illegally.

While abstinence is ineffective in drug dependency, other agents are needed in order to compromise the dependency. Products such as tetraethylthiuram disulfide; TETD (Antabuse) are used in sobriety programs, McNichol, R. W., Ewing, J. A., Faiman, M. D. Disulfiram (Antabuse): a unique medical aid to sobriety, Springfield, Ill., Thomas, 1987 and Mendelson, J. H., Mello, N. K., Eds, The Diagnosis and treatment of alcoholism, New York, McGraw-Hill, 1979, 204.

In U.S. Pat. No. 4,942,175 is described the use of a composition containing local anesthetics such as tetracaine, procaine and mixtures with suitable carriers. These agents can be used to treat cocaine addiction with a method called aversion therapy. In U.S. Pat. No. 4,948,803 is described the treatment of withdrawal symptoms resulting from addiction to a drug by treatment with azabicyclo indazole-3-carboxamides. In European Patent Application 90309062.9 published 06.03.91 is described a method of treating a chemical dependency in a mammal administering a compound (1S-cis)-4-(3,4-dichlorophenyl)-1,2,3,4-tetrahydro-N-m-ethyl-1-naphthalenamine, which is also known by the generic name of sertraline.

The most popular agent for the treatment of substance abuse is 4,4-diphenyl-6-dimethylamino-heptanone-3 hydrochloride also know as methadone. The principal actions of therapeutic value are analgesia and sedation and detoxification or maintenance in narcotic addiction.

SUMMARY OF THE INVENTION

It has been found that 1-(substituted-phenyl)-3-azabicyclo[3.1.0]hexanes of the formula:

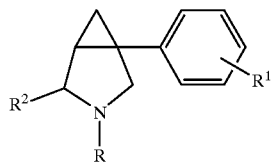

wherein R is hydrogen, alkyl ($C_1$–$C_6$); $R^1$ is hydrogen, mono or disubstituted halogen, alkoxy ($C_1$–$C_3$), $CF_3$, alkyl ($C_1$–$C_6$); and $R^2$ is hydrogen, methyl or ethyl, are useful for the prevention or relief of a withdrawal syndrome resulting from addiction to drugs or substances of abuse and for the treatment of chemical dependencies. Examples of chemical dependencies treatable by the method of the present invention are dependencies of alcohol, nicotine, cocaine, heroin, phenobarbitol and benzodiazepines.

It has also been found that 1-(substituted-phenyl)-3-azabicyclo[3.1.0]hexanes can inhibit the re-uptake of 5-hydroxytryptamine(5-HT), norepinephrine(NE) and dopamine(DA) in crude rat brain synaptosomal preparations, and may be useful, therefore, as agents for the treatment and relief of addictive behavior disorders such as, chemical substance abuse, eating disorders resulting in anorexia or obesity and other compulsive disorders.

DESCRIPTION OF THE PREFERRED EMBODIMENTS 1-(Substitutedphenyl)-3-azabicyclo[3.1.0]hexanes are useful for the treatment of chemical dependency in a mammal. In accordance with the above use, studies performed in the present invention indicate that 1-(3,4-dichlorophenyl)-3-azabicyclo[3.1.0]hexane hydrochloride reduces ethanol intake and ethanol preferences in rats without altering overall fluid intake.

Male Wistar rats are presented with an everyday free-choice between a 6% (v/v) ethanol solution and tap water. Following a seven-day baseline period, which establishes a pattern of stable drinking, only those animals whose consumption is greater than 50% of their total fluid intake are given intraperitoneal injections of three drugs. In part I citalopram (positive control) a neuronal serotonin uptake inhibitor at a dose of 30 mg/kg, and of 30 mg/kg, and 1-(3,4-dichlorophenyl)-3-azabicyclo[3.1.0]hexane hydrochloride, also a serotonin uptake inhibitor, at doses of 5, 10 and 20 mg/kg are given by intraperitoneal injection for seven days. In part II, animals are given intraperitoneal injections of diazepam at a dose of 10 mg/kg and again the positive control used is citalopram at 30 mg/kg. Treatment period for part II also is over a seven-day period. Following the seven-day treatment period, a post-treatment period which lasted for an additional seven days is conducted where the animals are presented with a free choice between ethanol and water in order to determine the rate of recovery of ethanol drinking. During baseline, drug treatment and post-treatment periods, ethanol consumption by the rats is calculated in terms of daily ethanol preference ratio (volume of ethanol per volume of total daily fluid intake) and in terms of daily absolute of ethanol ingested (g/kg body weight). Results obtained using 1-(3,4-dichlorophenyl)-3-azabicyclo [3.1.0]hexane hydrochloride reveal that it has a significant effect in attenuating voluntary ethanol consumption in rats.

EXPERIMENTAL METHOD

Subject Selection

Two hundred (200) drug-naive male Wistar rats obtained from the Canadian Breeding Farm Laboratories in Charles River Canada are used. All animals weigh between 180–200 g at the beginning of the experiment.

Housing and Maintenance

All animals are individually housed in stainless steel cages, in a room regulated for constant temperature, humidity and a 12-hour light/dark cycle (7:00 a.m.–7:00 p.m.). Each cage is equipped with two calibrated glass Richter tubes to deliver the fluids (ethanol and water) to the animals. All animals are presented with a free choice between ethanol and tap water throughout the experiment. The drinking vessels are randomly reversed in order to avoid bias generated by a position preference in the animals. In addition, Purina Rat Chow is made available throughout the experiment on an ad libitum basis.

At approximately the same time every day, 1300 h, the volume in mls of ethanol and tap water consumed by each animal is recorded. All tubes are then removed from the cages, rinsed and refilled with the appropriate fluids, i.e., ethanol solution and tap water. Also, all animals are weighed and their corresponding body weights recorded. At this time, additional food is provided.

Treatment Drugs

Citalopram, 1-(3,4-dichlorophenyl)-3-azabicyclo[3.1.0] hexane hydrochloride, diazepam.

Drugs used in part I are dissolved in Ringers solution to form the required doses. Drugs used in part II are suspended in a vehicle which consists of a 2% pre-boiled starch solution containing 5% polyethylene glycol 400 and tween 80 (1 drop/10 ml vehicle). All drugs are administered intraperitoneally according to the schedule (see Treatment period).

Part I (n=50)
  Group 1—Ringers solution (n=10)
  Group 2—citalopram 30 mg/kg (n=10)
  Group 3—1-(3,4-dichlorophenyl)-3-azabicyclo[3.1.0] hexane hydrochloride 5 mg/kg (n=10)
  Group 4—1-(3,4-dichlorophenyl)-3-azabicyclo[3.1.0] hexane hydrochloride 10 mg/kg (n=10)
  Group 5—1-(3,4-dichlorophenyl)-3-azabicyclo[3.1.0] hexane hydrochloride 20 mg/kg (n=10)

Part II (n=42)
  Group 1—vehicle (n=7)
  Group 2—citalopram 30 mg/kg (n=7)
  Group 3—diazepam 10 mg/kg (n=7)

Post-treatment period:—Upon cessation of the drug treatment period, the animals are presented with a free choice between 6% ethanol and tap water for an additional 7 days in order to determine the rate of recovery of ethanol drinking.

RESULTS—PART I

Ethanol Intake

All five treatment groups displayed a high level of ethanol consumption during the baseline period. During the treatment period, ethanol intake had decreased in all groups, with the most significant decrease observed in 1-(3,4-dichlorophenyl)-3-azabicyclo[3.1.0]hexane hydrohloride (20 mg/kg) group ($p<0.001$). The mean ethanol intake markedly dropped from the basal level of 3.79 g/kg to 1.13 g/kg during the treatment period. Cessation of treatment resulted in a marked increase in ethanol intake to 3.04 g/kg which is not significantly different from the Ringers group ($p>0.1$). Ethanol intake for the 1-(3,4-dichlorophenyl)-3-azabicyclo[3.1.0]hexane hydrochloride (5 mg/kg) group remained steady throughout the three periods. Although a slightly elevated ethanol intake is observed, it remained stable throughout all three periods and is not found to be significantly different from the control group. A more pronounced effect on ethanol consumption is that of citalopram and 1-(3,4-dichlorophenyl)-3-azabicyclo[3.1.0]hexane hydrochloride (10 mg/kg). Both appear to have almost the same effect in reducing ethanol intake. It appears that the 30 mg/kg dose of citalopram is approximately equipotent as a 10 mg/kg dose of 1-(3,4-dichlorophenyl)-3-azabicyclo [3.1.0]hexane hydrochloride. During post-treatment the animals in both citalopram and 1-(3,4-dichlorophenyl)-3-azabicyclo[3.1.0]hexane hydrochloride (10 mg/kg) groups increased their ethanol intake reflecting the drugs partial decrease and recovery in ethanol consumption.

Therefore, we can conclude that 1-(3,4-dichlorophenyl)-3-azabicyclo[3.1.0]hexane hydrochloride does attenuate ethanol consumption in rats. A 10 mg/kg dose resulting in a partial decrease in ethanol intake and 20 mg/kg resulting in a greater decrease in ethanol intake illustrating a dose-response relationship of 1-(3,4-dichlorophenyl)-3-azabicyclo[3.1.0]hexane hydrochloride.

Ethanol Preference

During the baseline period, all animals exhibit a high preference for ethanol over water. During the treatment period there is a slight but insignificant decrease in ethanol preference in the citalopram and 1-(3,4-dichlorophenyl)-3-azabicyclo[3.1.0]hexane hydrochloride (10 mg/kg) groups ($p>0.1$). If we examine the preference plot representations (treatment period), we observe a scattering of points which is common to both citalopram and 1-(3,4-dichlorophenyl)-3-azabicyclo[3.1.0]hexane hydrochloride (10 mg/kg). This would indicate that even though the mean preference did not significantly decrease, there is a partial effect, with a decrease in some rats but not others. During post-treatment there is a trend towards increasing ethanol preference in both citalopram and 1-(3,4-dichlorophenyl)-3-azabicyclo[3.1.0] hexane hydrochloride (10 mg/kg) groups as can be observed in the quartile plot representations (a shift from lowest to next higher quartile).

The 1-(3,4-dichlorophenyl)-3-azabicyclo[3.1.0]hexane hydrochloride (5 mg/kg) group displayed a stable mean preference throughout all three periods and is not significantly different from the Ringers control group. This would indicate that a 5 mg/kg dose of 1-(3,4-dichlorophenyl)-3-azabicyclo[3.1.0]hexane hydrochloride has no effect on ethanol preference, perhaps due to being a sub-threshold dose. At a dose of 20 mg/kg, 1-(3,4-dichlorophenyl)-3-azabicyclo[3.1.0]hexane hydrochloride has a significant effect in decreasing ethanol preference ($p<0.01$) during treatment period. The mean preference level during baseline is 67.94%, but during treatment has dropped significantly to 25.55%. Cessation of treatment does result in a near complete recovery of ethanol preference to 58.66%, which is not significantly different from post-treatment control value. Therefore, we can conclude that 1-(3,4-dichlorophenyl)-3-azabicyclo[3.1.0]hexane hydrochloride (5 and 10 mg/kg) and citalopram (30 mg/kg) do not have a statistically significant effect to decrease ethanol preference, though there is a partial effect with citalopram and 1-(3,4-dichlorophenyl)-3-azabicyclo[3.1.0]hexane hydrochloride (10 mg/kg). At a dose of 20 mg/kg, 1-(3,4-dichlorophenyl)-3-azabicyclo [3.1.0]hexane hydrochloride is found to be very effective, having a significant effect to decrease ethanol preference.

Total Fluid Intake

During the baseline period, all animals display a stable total fluid intake level ranging from 116.16–127.90 ml/kg/day. A slight drop in the total fluid intake during the treatment period is observed in all five groups, but is found to be statistically insignificant in the 1-(3,4-dichlorophenyl)-

3-azabicyclo[3.1.0]hexane hydrochloride 5, 10, 20 mg/kg groups relative to the Ringers control group (p>0.1). The greatest decrease in total fluid intake is observed in a citalopram group.

The citalopram group had a mean total fluid intake level, during the treatment period of 82.70 ml/kg/day, significantly (p<0.01) lower than the Ringers control group, whereas the remaining three groups are not significantly different from the control values (p>0.1). Furthermore, the slight decrease in the total fluid intake, during treatment, of all groups (except citalopram) did not differ greatly from the post-treatment fluid intake values. This indicates that there is a relatively stable total fluid intake level throughout baseline, treatment and post-treatment periods demonstrating that 1-(3,4-dichlorophenyl)-3-azabicyclo[3.1.0]hexane hydrochloride at doses of 5, 10, 20 mg/kg has no effect on total fluid intake. In contrast, fluid intake for the citalopram group increased sharply during post-treatment returning to basal level and clearly demonstrating citalopram's effect on total fluid intake. 1-(3,4-Dichlorophenyl)-3-azabicyclo[3.1.0] hexane hydrochloride at doses as high as 20 mg/kg does not have a significant effect on total fluid intake.

Food Intake

All rats during baseline exhibit a stable food consumption level with a mean value of 20.24 g/day for the five treatment groups. During the treatment period, food consumption decreased in all five groups, with the greatest decrease observed in the citalopram and 1-(3,4-dichlorophenyl)-3-azabicyclo[3.1.0]hexane hydrochloride (20 mg/kg) groups. The decrease in food intake for the 1-(3,4-dichlorophenyl)-3-azabicyclo[3.1.0]hexane hydrochloride 5 and 10 mg/kg groups is found to be insignificant relative to the control group (p>0.05), but there is a significant decrease in food consumption in.the citalopram and 1-(3,4-dichlorophenyl)-3-azabicyclo[3.1.0]hexane hydrochloride (20 mg/kg) groups (p<0.05). The decrease in food consumption for the citalopram and 1-(3,4-dichlorophenyl)-3-azabicyclo[3.1.0] hexaned hydrochloride (20 mg/kg) groups may be indicative of the drugs effect on other neuronal systems which regulate food consumption. During post-treatment, the two groups which most affected food intake (i.e. citalopram, 1-(3,4-dichlorophenyl)-3-azabicyclo[3.1.0]hexane hydrochloride (20 mg/kg) have reestablished food intake levels back to pretreatment consumption levels and are not differing significantly from the control group (p>0.1). Therefore, we can conclude that 1-(3,4-dichlorophenyl)-3-azabicyclo[3.1.0] hexane hydrochloride at a dose of 20 mg/kg does have an anorexic effect similar to a 30 mg/kg dose of citalopram.

CONCLUSIONS

The results of this experiment clearly show that 1-(3,4-dichlorophenyl)-3-azabicyclo[3.1.0]hexane hydrochloride, a selective 5-HT reuptake inhibitor, does produce an attenuation in ethanol consumption in rats. A dose-response relationship is evident with 5 mg/kg resulting in no response, 10 mg/kg resulting in a modest decrease in ethanol consumption and a 20 mg/kg dose producing a very marked and significant attenuation in ethanol consumption. Upon cessation of treatment, ethanol consumption had returned close to basal levels.

At a dose of 20 mg/kg, 1-(3,4-dichlorophenyl)-3-azabicyclo[3.1.0]hexane hydrochloride has an insignificant effect on total fluid intake, therefore, indicating that the decrease in ethanol intake is compensated for through increased water intake. 1-(3,4-Dichlorophenyl)-3-azabicyclo[3.1.0]hexane hydrochloride did display a modest anorexic effect during the treatment phase similar to that of citalopram, perhaps due to the drugs effect on other neuronal systems which regulate food intake. 1-(3,4-Dichlorophenyl)-3-azabicyclo[3.1.0]hexane hydrochloride is more potent than citalopram, with 1-(3,4-dichlorophenyl)-3-azabicyclo[3.1.0]hexane hydrochloride (10 mg/kg) producing about the same effect on ethanol consumption as a 30 mg/kg dose of citalopram, but without a significant effect on food intake at the 10 mg/kg dose. 1-(3,4-Dichlorophenyl)-3-azabicyclo[3.1.0]hexane hydrochloride at the 20 mg/kg dose resulted in a substantial decrease in ethanol intake with insignificant effects on total fluid intake, but did cause a modest decrease in food intake. The results obtained with 1-(3,4-dichlorophenyl)-3-azabicyclo[3.1.0]hexane hydrochloride give further evidence for the relationship between increased 5-HT levels in the brain and the resulting attenuation in ethanol consumption. The ability of 1-(3,4-dichlorophenyl)-3-azabicyclo[3.1.0]hexane hydrochloride to attenuate ethanol consumption is evident.

| | Baseline ($\bar{x}$ ± S.D.) | Treatment ($\bar{x}$ ± S.D.) | Post-Treatment ($\bar{x}$ ± S.D.) |
|---|---|---|---|
| Ethanol Intake (g/kg body weight) | | | |
| Ringers | 4.26 ± 0.95 | 3.43 ± 1.57 | 3.55 ± 1.51 |
| Citalopram | 4.49 ± 1.18 | 2.34 ± 1.44 | 3.32 ± 1.86 |
| *(5 mg/kg) | 5.02 ± 1.16 | 4.13 ± 0.93 | 4.86 ± 1.78 |
| *(10 mg/kg) | 4.55 ± 0.90 | 2.60 ± 1.44 | 2.99 ± 1.42 |
| *(20 mg/kg) | 3.80 ± 1.00 | 1.13 ± 0.72 | 3.04 ± 1.34 |
| Ethanol Preference (%) | | | |
| Ringers | 75.00 ± 13.34 | 65.04 ± 27.03 | 66.00 ± 25.92 |
| Citalopram | 75.78 ± 18.09 | 61.06 ± 35.09 | 57.81 ± 32.23 |
| *(5 mg/kg) | 83.67 ± 14.58 | 81.29 ± 17.38 | 82.39 ± 20.87 |
| *(10 mg/kg) | 75.05 ± 16.53 | 51.66 ± 33.48 | 55.90 ± 28.51 |
| *(20 mg/kg) | 67.94 ± 17.05 | 25.55 ± 17.28 | 58.66 ± 23.98 |
| Total Fluid Intake (ml/kg/day) | | | |
| Ringers | 118.29 ± 9.85 | 109.02 ± 15.49 | 111.15 ± 15.48 |
| Citalopram | 124.19 ± 12.35 | 82.70 ± 9.45 | 121.47 ± 14.98 |
| *(5 mg/kg) | 124.65 ± 12.61 | 105.85 ± 11.92 | 120.60 ± 21.86 |
| *(10 mg/kg) | 127.90 ± 15.88 | 112.25 ± 22.06 | 115.41 ± 15.56 |
| *(20 mg/kg) | 116.16 ± 10.33 | 96.60 ± 33.91 | 107.22 ± 11.96 |
| Food Consumption (g/day) | | | |
| Ringers | 20.60 ± 0.91 | 18.80 ± 1.32 | 20.30 ± 1.56 |
| Citalopram | 20.14 ± 1.71 | 11.96 ± 3.56 | 21.47 ± 1.94 |
| *(5 mg/kg) | 19.74 ± 1.65 | 17.17 ± 1.31 | 19.50 ± 1.41 |
| *(10 mg/kg) | 20.43 ± 1.55 | 16.96 ± 1.98 | 21.32 ± 1.96 |
| *(20 mg/kg) | 20.28 ± 1.12 | 13.31 ± 1.86 | 20.88 ± 2.08 |

*1-(3,4-dichlorophenyl)-3-azabicyclo[3.1.0]hexane hydrochloride

| ANOVA on Post-Treatment Period | | | | | |
|---|---|---|---|---|---|
| Source | S.S. | D.F. | M.S. | F | P |
| 1. Ethanol Intake | | | | | |
| Error | 114.70 | 45 | 2.55 | — | — |
| Group | 23.50 | 4 | 5.87 | 2.30 | 0.073 |
| 2. Preference | | | | | |
| Error | 31805.53 | 45 | 706.79 | — | — |
| Group | 4745.10 | 4 | 1186.27 | 1.68 | 0.172 |
| 3. Total Fluid Intake | | | | | |
| Error | 11944.66 | 45 | 265.44 | — | — |
| Group | 1484.78 | 4 | 371.19 | 1.40 | 0.250 |
| 4. Food Intake | | | | | |
| Error | 147.7 | 45 | 3.27 | — | — |
| Group | 26.01 | 4 | 6.50 | 1.99 | 0.112 |

| Duncan's Multiple Range Test for Ethanol Preference | | | | | |
|---|---|---|---|---|---|
| | Ringers | Citalopram | **(5 mg/kg) | **(10 mg/kg) | **(20 mg/kg) |
| Difference Score - Treatment | | | | | |
| Ringers | — | n.s. | n.s. | n.s. | * |
| Citalopram | n.s. | — | n.s. | n.s. | * |
| **(5 mg/kg) | n.s. | n.s. | — | * | * |
| **(10 mg/kg) | n.s. | n.s. | * | — | * |
| **(20 mg/kg) | * | * | * | * | — |
| Difference Score - Post-Treatment | | | | | |
| Ringers | — | n.s. | n.s. | n.s. | n.s. |
| Citalopram | n.s. | — | n.s. | n.s. | n.s. |
| **(5 mg/kg) | n.s. | n.s. | — | n.s. | n.s. |
| **(10 mg/kg) | n.s. | n.s. | n.s. | — | n.s. |
| **(20 mg/kg) | n.s. | n.s. | n.s. | n.s. | — |

*denotes pairs of groups significantly different at p F 0.05 level
n.s. denotes non-significant differences
**1-(3,4-dichlorophenyl)-3-azabicyclo[3.1.0]hexane hydrochloride

| Individual t-Test with Ringers - Treatment Period | | |
|---|---|---|
| | t-Value | P |
| Ethanol Intake | | |
| Citalopram | −1.93 | 0.060 |
| *(5 mg/kg) | 1.23 | 0.225 |
| *(10 mg/kg) | −1.47 | 0.148 |
| *(20 mg/kg) | −4.07 | 0.000 |
| Ethanol Preference | | |
| Citalopram | −0.33 | 0.745 |
| *(5 mg/kg) | 1.34 | 0.187 |
| *(10 mg/kg) | −1.10 | 0.276 |
| *(20 mg/kg) | −3.25 | 0.002 |
| Total Fluid Intake | | |
| Citalopram | −2.87 | 0.006 |
| *(5 mg/kg) | −0.34 | 0.731 |
| *(10 mg/kg) | 0.35 | 0.727 |
| *(20 mg/kg) | −1.02 | 0.310 |
| Ethanol Preference | | |
| Citalopram | −7.06 | 0.000 |
| *(5 mg/kg) | −1.68 | 0.100 |
| *(10 mg/kg) | −1.90 | 0.064 |
| *(20 mg/kg) | −5.66 | 0.000 |

*1-(3,4-dichlorophenyl)-3-azabicyclo[3.1.0]hexane hydrochloride

| Individual t-Test with Ringers - Post-Treatment Period | | |
|---|---|---|
| | t-Value | P |
| Ethanol Intake | | |
| Citalopram | −0.32 | 0.748 |
| *(5 mg/kg) | 1.84 | 0.073 |
| *(10 mg/kg) | −0.78 | 0.437 |
| *(20 mg/kg) | −0.71 | 0.479 |
| Ethanol Preference | | |
| Citalopram | −0.69 | 0.495 |
| *(5 mg/kg) | 1.38 | 0.175 |
| *(10 mg/kg) | −0.85 | 0.400 |
| *(20 mg/kg) | −0.62 | 0.540 |
| Total Fluid Intake | | |
| Citalopram | 1.41 | 0.164 |
| *(5 mg/kg) | 1.30 | 0.201 |
| *(10 mg/kg) | 0.58 | 0.562 |
| *(20 mg/kg) | −0.54 | 0.592 |
| Ethanol Preference | | |
| Citalopram | 1.44 | 0.156 |
| *(5 mg/kg) | −0.99 | 0.328 |
| *(10 mg/kg) | 1.26 | 0.215 |
| *(20 mg/kg) | 0.72 | 0.474 |

*1-(3,4-dichlorophenyl)-3-azabicyclo[3.1.0]hexane hydrochloride

RESULTS—PART II

Ethanol Intake

All six treatment groups displayed a high level of ethanol consumption during the baseline period. During the treatment period, all groups showed a slight, but insignificant change in ethanol intake relative to the control group (p>0.1). The largest decrease in ethanol consumption occurred in the citalopram group. Although statistically insignificant, it does indicate a partial effect by citalopram consistent with observations made in part I. In contrast, the diazepam group shows relatively little change in ethanol intake throughout the baseline/treatment/post-treatment periods. This stable level of ethanol consumption allows us to conclude that diazepam at 10 mg/kg has no effect on ethanol intake in rats.

Ethanol Preference

During the baseline period, all six treatment groups exhibit a high preference for ethanol over water. During the treatment period all groups demonstrate a slight, but insignificant change in preference relative to the control group (p>0.1). Once again, the largest decrease in ethanol preference occurred in the citalopram group. During the treatment period ethanol preference dropped to 69.17% from 86.16%, a decrease consistently observed with a 30 mg/kg dose of citalopram (i.e. part I). The diazepam group demonstrated virtually no change throughout all three periods indicating a lack of an effect on ethanol preference.

Total Fluid Intake

During the baseline period, all animals display a stable total fluid intake level, ranging from 106.97–117.70 ml/kg/day. During treatment, a drop in total fluid intake is observed in all groups, but is found to be statistically insignificant relative to the control group (p>0.05). The largest decrease in total fluid intake is recorded in the citalopram group, from 117.70 ml/kg/day to 86.79 ml/kg/day, a decrease very close to the significant level (p=0.05). This indicates that citalopram does result in a partial decrease in both ethanol and water intake. Furthermore, the relatively large decrease in total fluid intake recovered back to baseline level during post-treatment. In contrast, there is only a very slight difference between treatment and post-treatment total fluid intake values for the diazepam groups. Therefore, it can be concluded that diazepam (10 mg/kg) does not affect total fluid intake.

Food Intake

All rats during the baseline period exhibit a stable food intake level, with a mean value of 20.66 g/day for the six groups. Food consumption for all groups (except citalopram) remained virtually the same throughout baseline/treatment/post-treatment periods. This indicates that diazepam at 10 mg/kg has no effect on food intake. A significant decrease in food intake did occur in the citalopram group (p<0.001). Food intake drops to 14.20 g/day, approximately 25% lower than baseline level, during treatment with citalopram. During post-treatment, food intake returned back to original baseline levels.

CONCLUSIONS

The results of this experiment reveal that diazepam at 10 mg/kg has no effect to attenuate voluntary ethanol consumption in rats. These result would allow us to rule out any interaction between benzodiazepine receptor mechanisms and an attenuation in ethanol consumption. Since these agents are void of any effect on 5-HT re-uptake mechanisms the lack of effect to attenuate ethanol consumption might have been predictable. Interestingly, the sedation which is observed or the diazepam did not result in any decrease in total fluid intake or food intake, a decrease which might have been predicted from drugs with sedating properties. Therefore, based on the results of this experiment, we conclude that diazepam did not attenuate ethanol consumption.

|  | Baseline ($\bar{x}$ ± S.D.) | Treatment ($\bar{x}$ ± S.D.) | Post-Treatment ($\bar{x}$ ± S.D.) |
|---|---|---|---|
| Ethanol Intake (g/kg body weight) | | | |
| Vehicle | 3.75 ± 1.92 | 3.82 ± 1.28 | 4.15 ± 1.53 |
| Citalopram | 4.86 ± 1.09 | 2.95 ± 1.59 | 3.87 ± 1.91 |
| Diazepam (10 mg/kg) | 3.92 ± 1.75 | 3.48 ± 1.51 | 3.95 ± 1.91 |
| Ethanol Preference (%) | | | |
| Vehicle | 70.08 ± 26.82 | 79.09 ± 19.25 | 79.69 ± 23.28 |
| Citalopram | 86.16 ± 14.74 | 69.17 ± 30.25 | 68.90 ± 29.38 |
| Diazepam (10 mg/kg) | 73.21 ± 26.62 | 72.76 ± 28.03 | 72.15 ± 27.34 |
| Total Fluid Intake (ml/kg/day) | | | |
| Vehicle | 107.35 ± 17.15 | 99.14 ± 12.20 | 107.91 ± 14.64 |
| Citalopram | 117.70 ± 11.00 | 86.79 ± 13.15 | 114.14 ± 11.94 |
| Diazepam (10 mg/kg) | 111.17 ± 11.23 | 99.03 ± 8.85 | 111.57 ± 19.38 |
| Food Consumption (g/day) | | | |
| Vehicle | 21.33 ± 2.58 | 19.94 ± 2.14 | 19.86 ± 1.76 |
| Citalopram | 19.82 ± 1.87 | 14.20 ± 2.76 | 19.86 ± 2.26 |
| Diazepam (10 mg/kg) | 21.24 ± 1.94 | 20.75 ± 2.04 | 20.98 ± 2.24 |

| Individual t-Test with Vehicle - Treatment Period | | |
|---|---|---|
|  | t-Value | P |
| Ethanol Intake | | |
| Citalopram | −1.10 | 0.277 |
| Diazepam | −0.43 | 0.666 |
| Ethanol Preference | | |
| Citalopram | −0.68 | 0.500 |
| Diazepam | −0.43 | 0.666 |
| Total Fluid Intake | | |
| Citalopram | −1.84 | 0.075 |
| Diazepam | −0.01 | 0.988 |
| Ethanol Preference | | |
| Citalopram | −4.79 | 0.000 |
| Diazepam | 0.68 | 0.499 |

| Individual t-Test with Vehicle - Treatment Period | | |
|---|---|---|
|  | t-Value | P |
| Ethanol Intake | | |
| Citalopram | −1.10 | 0.277 |
| Diazepam | −0.43 | 0.666 |
| Ethanol Preference | | |
| Citalopram | −0.68 | 0.500 |
| Diazepam | −0.43 | 0.666 |
| Total Fluid Intake | | |
| Citalopram | −1.84 | 0.075 |
| Diazepam | −0.01 | 0.988 |

-continued

| Individual t-Test with Vehicle - Treatment Period | | |
|---|---|---|
| | t-Value | P |
| Ethanol Preference | | |
| Citalopram | −4.79 | 0.000 |
| Diazepam | 0.68 | 0.499 |

1-(Substitutedphenyl)-3-azabicyclo[3.1.0]hexanes inhibit the neuronal reuptake of 5-HT, NE and DA in rat brain crude synaptosomal preparations at concentrations consistent with the ability to serve as agents for the treatment of addictive behaviors such as: substance abuse, eating disorders resulting in obesity, and other compulsive disorders.

In accordance with the above usefulness, studies are performed to measure the ability of 1-(substitutedphenyl)-3-azabicyclo[3.1.0]hexanes to inhibit the reuptake of 5-HT, NE, and DA in rat brain synaptosomal preparations.
Inhibition of Rat Synaptosomal Uptake of Norepinephrine (NE), Serotonin (5-HT) and Dopamine (DA)
Methods Male Wistar rats weighing approximately 180–200 g are decapitated and their brains rapidly removed and dissected according to the method of Glowinski and Iversen. Glowinski, J. and Iversen, L. L., Regional studies of catecholamines in the rat brain I. The disposition of 3H-norepinephrine, 3H-dopamine and 3H-DOPA in various regions of the brain. J. Neurochem. 13:655–669, 1966. Striatal tissues are pooled from three rat brains for the uptake of 3H-dopamine (3H-DA) and diencephalic-mid brain areas were used for the uptake of 3H-norepinephrine (3H-NE) and 3H-serotonin (3H-5HT). The tissues are immediately weighed and homogenized with a teflon-glass pestle homogenizer in 10 volumes of ice cold 0.32 M sucrose. The homogenates are centrifuged at 4° C. at 900×g for 10 minutes to remove nuclear particles and cellular debris. The supernatants are carefully withdrawn and transferred into clean test tubes kept in ice. Aliquots of these preparations containing crude synaptic nerve endings are used in subsequent uptake studies.

Amine uptake in crude synaptosomes is determined by a method essentially the same as that described by Snyder and Coyle, Snyder, S. H. and Coyle, J. T. Regional differences in 3H-norepinephrine and 3H-dopamine uptake into rat brain homogenates. J. Pharmacol. Exp. Ther. 165:78–86, 1969. Briefly, a 0.1 ml aliquot of the above tissue preparation is added to test tubes containing 3.7 ml of Krebs-Ringer phosphate buffer pH 7.4 with glucose (2 mg/ml), calcium chloride 0.024%, ascorbic acid (0.2 mg/ml) and nialamide (1.24×10−5M). 1-(3,4-Dichlorophenyl)-3-azabicyclo[3.1.0] hexane hydrochloride at varying concentrations (0.01–2.5 μM) is added in a 0.1 ml volume. The incubation mixtures are agitated at 37° C. for 10 minutes under an atmosphere of 95% oxygen and 5% $CO_2$ in a Dubnoff metabolic shaker to ensure irreversible inhibition of monoamine oxidase (MAO). After this initial pre-incubation period, the tubes are returned to the ice bath. 3H-DA, 3H-NE or 3H-5HT is added in a 0.1 ml volume to give a final concentration of labeled amine of 2×10−8 M, and the incubation at 37° C. is continued for an additional 4 min. A set of tubes serving as control (uptake at 0° C.) is left in an ice bath. After the final incubation period, the samples are cooled in ice and then centrifuged at 4° C. at 10,000×g. The supernatant fluid is gently poured off from each tube. The surface of the pellet of each sample is washed with 5 ml of ice cold 0.9% sodium chloride which is then aspirated off without disturbing the pellet. The pellet is resuspended in a cintillation fluid ad radioactivity was determined. Protein content in the tissue samples is determined by the method of Lowry et al. Lowry, O. H., Rosebrough, N. J., Farr, A. L. and Randall, R. J. Protein measurement with the folin reagent. J. Biol. Chem. 193:265, 1951. The concentration of drug which inhibits the uptake of the labeled amine by 50% is determined by Hill analysis of the data.

Table I

Inhibition of Norepinephrine (NE), Serotonin (5-MT) and Dopamine (DA) in Rat Brain Synaptosomes

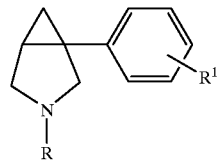

| | | Inhibition of Reuptake $IC_{50}$ (nM) | | |
|---|---|---|---|---|
| R | $R^1$ | NE | 5-HT | DA |
| ±H | p-Cl | 274 | 169 | — |
| +H | p-Cl | 279 | 55 | — |
| ±H | H | 401 | 470 | — |
| ±H | 3-Br-4-$OCH_3$ | 318 | 260 | — |
| ±H | p-$CH_3$ | 741 | 137 | 2364 |
| ±H | p-F | — | 811 | — |
| +H | p-$CH_3$ | 215 | 96 | — |
| ±H | 3,4-di Cl | 145 | 26 | 232 |

A 1-(substitutedphenyl)-3-azabicyclo[3.1.0]hexane or a pharmaceutically acceptable salt thereof, when used to treat a chemical dependency, may be administered either orally or parenterally. It is generally administered in dosages ranging from about 50–200 mg per day, although variations will necessarily occur depending upon the condition of the subject being treated and the particular route of administration chosen. It may be administered either alone or in combination with pharmaceutically acceptable carriers by either of the above routes, and such administration can be carried out in both single and multiple dosages. More particularly, a 1-(substitutedphenyl)-3-azabicyclo[3.1.0] hexane or a pharmaceutically acceptable salt thereof, may be administered in a wide variety of different dosage forms, i.e., it may be combined with various pharmaceutically acceptable inert carriers in the form of tablets, capsules, lozenges, troches, hand candies, powders, sprays, aqueous suspensions, injectable solutions, elixirs, syrups and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, a 1-(substitutedphenyl)-3-azabicyclo[3.1.0] hexane or a pharmaceutically acceptable salt thereof, when used to treat a chemical dependency, is present in such forms at concentration levels ranging from about 0.5% to about 90% by weight of the total composition, i.e., in amounts that are sufficient to provide the desired unit dosage. It may exist in different polymorphic forms, i.e. different crystalline forms.

For purpose of oral administration, tablets containing various excipients such as sodium citrate, calcium carbonate and calcium phosphate may be employed along with various disintegrants such as starch, preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred fillers would also include lactose or milk sugar as well as highly molecular weight polyethylene glycols. When aqueous suspensions and/or elixiers are desired for oral administration, the 1-(substitutedphenyl)-3-azabicyclo[3.1.0]hexane or pharmaceutically acceptable salt thereof, may be combined with various sweetening or flavoring agents, coloring matter or dyes and, if so desired, emulsifying and/or suspending agents, together with diluents such as water, ethanol, propylene glycol, glycerin and various like combinations thereof.

For purposes of parenteral administration, solutions of 1-(substitutedphenyl)-3-azabicyclo[3.1.0]hexane, or a pharmaceutically acceptable salt thereof, in sesame or peanut oil or in aqueous propylene glycol or N,N-dimethylformamide may be employed, as well as sterile aqueous solutions of the water-soluble, non-toxic mineral and organic acid addition salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

We claim:

1. A method for treatment of an addictive, compulsive disorder caused by alcohol or cocaine abuse, which comprises the administration to a human or animal suffering from such a disorder, an effective amount of the compound of the formula:

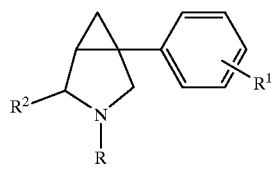

in which R is hydrogen or alkyl of 1–6 carbon atoms;
R$^1$ is hydrogen or one or two substituents selected from the halogens, alkoxy of 1 to 3 carbon atoms, CF$_3$ or alkyl of 1–6 carbon atoms; and
R$^2$ is hydrogen, methyl or ethyl;
or a pharmaceutically acceptable salt thereof.

2. A method of treatment for cocaine abuse according to claim 1.

3. The method according to claim 1, wherein the compound is (±)-1-(3,4-dichlorophenyl)-3-azabicyclo[3.1.0]hexane hydrochloride.

4. The method according to claim 1, wherein the compound is (±)-1-(4-methylphenyl)-3-azabicyclo[3.1.0]hexane hydrochloride.

5. The method according to claim 1, wherein the compound is (+)-1-(4-methylphenyl)-3-azabicyclo[3.1.0]hexane hydrochloride.

6. The method according to claim 1, wherein the compound is (±)-1-(4-chlorophenyl)-3-azabicyclo[3.1.0]hexane hydrochloride.

7. The method according to claim 1, wherein the compound is (+)-1-(4-chlorophenyl)-3-azabicyclo[3.1.0]hexane hydrochloride.

8. The method according to claim 1, wherein the compound is (±)-1-phenyl-3-azabicyclo[3.1.0]hexane hydrochloride.

9. The method according to claim 1, wherein the compound is (±)-1-(3-bromo-4-methoxyphenyl)-3-azabicyclo[3.1.0]hexane hydrochloride.

10. The method according to claim 1, wherein the compound is (±)-1-(4-fluorophenyl)-3-azabicyclo[3.1.0]hexane hydrochloride.

11. A method for treatment of cocaine abuse according to claims 3, 4, 5, 6, 7, 8, 9 or 10.

12. A method for treatment of drug dependence caused by alcohol or cocaine abuse, which comprises administering to a human or animal suffering from or dependent on a drug, an effective amount of the compound of the formula:

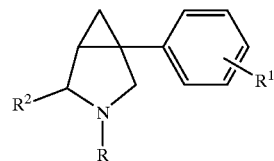

in which R is hydrogen or alkyl of 1–6 carbon atoms;
R$^1$ is hydrogen or one or two substituents selected from the halogens, alkoxy of 1 to 3 carbon atoms, CF$_3$ or alkyl of 1–6 carbon atoms; and
R$^2$ is hydrogen, methyl or ethyl;
or a pharmaceutically acceptable salt thereof.

13. A method of treatment of dependence on cocaine according to claim 12.

14. The method according to claim 12, wherein the compound is (±)-1-(3,4-dichlorophenyl)-3-azabicyclo[3.1.0]hexane hydrochloride.

15. The method according to claim 12, wherein the compound is (±)-1-(4-methylphenyl)-3-azabicyclo[3.1.0]hexane hydrochloride.

16. The method according to claim 12, wherein the compound is (+)-1-(4-methylphenyl)-3-azabicyclo[3.1.0]hexane hydrochloride.

17. The method according to claim 12, wherein the compound is (±)-1-(4-chlorophenyl)-3-azabicyclo[3.1.0]hexane hydrochloride.

18. The method according to claim 12, wherein the compound is (+)-1-(4-chlorophenyl)-3-azabicyclo[3.1.0]hexane hydrochloride.

19. The method according to claim 12, wherein the compound is (±)-1-phenyl-3-azabicyclo[3.1.0]hexane hydrochloride.

20. The method according to claim 12, wherein the compound is (±)-1-(3-bromo-4-methoxyphenyl)-3-azabicyclo[3.1.0]hexane hydrochloride.

21. The method according to claim 12, wherein the compound is (±)-1-(4-fluorophenyl)-3-azabicyclo[3.1.0]hexane hydrochloride.

22. A method of treatment of dependence on cocaine according to claims 14, 15, 16, 17, 18, 19, 20, or 21.

23. A method for treatment of an addictive, compulsive disorder caused by alcohol abuse, which comprises the administration to a human or animal suffering from such a disorder, an effective amount of the compound of the formula:

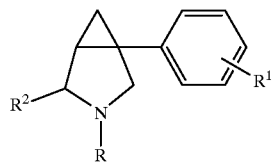

in which R is hydrogen or alkyl of 1–6 carbon atoms;
R$^1$ is hydrogen or one or two substituents selected from the halogens, alkoxy of 1 to 3 carbon atoms, CF$_3$ or alkyl of 1–6 carbon atoms; and
R$^2$ is hydrogen, methyl or ethyl;
or a pharmaceutically acceptable salt thereof.

24. The method of claim 23 in which said compound is selected from the group consisting of:

(±)-1-(3,4-dichlorophenyl)-3-azabicyclo[3.1.0]hexane;
(±)-1-(4-methylphenyl)-3-azabicyclo[3.1.0]hexane;
(+)-1-(4-methylphenyl)-3-azabicyclo[3.1.0]hexane;
(±)-1-(4-chlorophenyl)-3-azabicyclo[3.1.0]hexane;
(+)-1-(4-chlorophenyl)-3-azabicyclo[3.1.0]hexane;
(±)-1-phenyl-3-azabicyclo[3.1.0]hexane;
(±)-1-(3-bromo-4-methoxyphenyl)-3-azabicyclo[3.1.0]hexane;
and (±)-1-(4-fluorophenyl)-3-azabicyclo[3.1.0]hexane;
or a pharmaceutically acceptable salt thereof.

* * * * *